(12) United States Patent
Malekafzali

(10) Patent No.: US 7,456,938 B2
(45) Date of Patent: Nov. 25, 2008

(54) LASER MICRODISSECTION ON INVERTED POLYMER FILMS

(75) Inventor: Ashi Malekafzali, Rancho Palos Verdes, CA (US)

(73) Assignee: MDS Analytical Technologies (US) Inc., Sunnyvale, CA (US)

( * ) Notice: Subject to any disclaimer, the term of this patent is extended or adjusted under 35 U.S.C. 154(b) by 618 days.

(21) Appl. No.: 10/982,230

(22) Filed: Nov. 4, 2004

(65) Prior Publication Data

US 2006/0023201 A1 Feb. 2, 2006

Related U.S. Application Data

(60) Provisional application No. 60/518,029, filed on Nov. 7, 2003.

(51) Int. Cl.
*G01N 1/00* (2006.01)
(52) U.S. Cl. ............................. 356/36; 435/4; 435/40.5
(58) Field of Classification Search ................... 356/36; 435/4, 40.5
See application file for complete search history.

(56) References Cited

U.S. PATENT DOCUMENTS

| | | | |
|---|---|---|---|
| 5,859,699 A * | 1/1999 | Baer et al. | |
| 5,985,085 A * | 11/1999 | Baer et al. | |
| 6,157,446 A * | 12/2000 | Baer et al. | |
| 6,184,973 B1 * | 2/2001 | Baer et al. | |
| 6,215,550 B1 * | 4/2001 | Baer et al. | |
| 6,469,779 B2 * | 10/2002 | Baer et al. | |
| 6,495,195 B2 * | 12/2002 | Baer et al. | |
| 6,512,576 B1 * | 1/2003 | Baer et al. | |
| 6,528,248 B2 * | 3/2003 | Lossing et al. | |
| 6,690,470 B1 * | 2/2004 | Baer et al. | |
| 6,867,038 B2 * | 3/2005 | Liotta et al. | 435/325 |
| 7,221,447 B2 * | 5/2007 | Baer et al. | 356/244 |
| 2001/0038449 A1 * | 11/2001 | Baer et al. | |
| 2002/0090122 A1 * | 7/2002 | Baer et al. | |
| 2004/0093166 A1 * | 5/2004 | Kil | |
| 2006/0087643 A1 * | 4/2006 | Donovan et al. | 356/36 |
| 2006/0134692 A1 * | 6/2006 | Emmert-Buck et al. | 435/7.1 |
| 2006/0172278 A1 * | 8/2006 | Bonner et al. | 435/4 |

FOREIGN PATENT DOCUMENTS

WO WO2002/057746 * 7/2002

OTHER PUBLICATIONS

Suarez-Quian C. et al. Laser Capture Microdissection of Single Cells from Complex Tissues. Bio Techiques 26(2)328-335; 1999.*

Emmert-Buck et al., "Laser Capture Microdissection," Science 274(5289) 998-1001 (1996).*

* cited by examiner

*Primary Examiner*—Ralph Gitomer
(74) *Attorney, Agent, or Firm*—Fish & Richardson P.C.

(57) ABSTRACT

Systems and methods for automated laser microdissection are disclosed. A sample of biological material is located between a polymer membrane and a substrate. Targeted biological material is manually or automatically selected and a transfer film is placed in juxtaposition with the targeted biological material on the side of the polymer membrane. An infrared laser activates at least a portion of the transfer film such that the transfer film in the vicinity of targeted portion of biological material adheres onto the polymer membrane. The infrared laser is directed in a closed or substantially closed curve around the targeted portions or directly at the targeted portions. The transfer film is then separated removing the targeted portions of biological material which are adhered along with the membrane from the remaining portion of the tissue sample.

27 Claims, 11 Drawing Sheets

LASER MICRODISSECTION ON INVERTED POLYMER FILMS

CROSS-REFERENCE TO RELATED APPLICATIONS

This application claims priority to U.S. Provisional Application Ser. No. 60/518,029, entitled "Laser capture microdissection on inverted polymer films," filed on Nov. 7, 2003 which is incorporated herein by reference in its entirety.

FIELD OF THE INVENTION

The invention relates generally to the field of laser microdissection. More particularly, the invention relates to microdissecting targeted regions of biological material from a tissue sample.

BACKGROUND

Tissue biopsies are frequently obtained for diagnostic and therapeutic purposes. Typically, a tissue biopsy sample consists of a 5 to 10 micron slice of tissue that is placed on a glass microscope slide using techniques well known in the field of pathology. The tissue sample will typically consist of a variety of different types of cells. Often a pathologist will desire to remove only a small portion of the tissue for further analysis. Before the advent of laser microdissection, pathologists would have to resort to various time-consuming and imprecise microdissection techniques to obtain a sample of the desired region of a biopsy. Laser microdissection provides a simple method for the procurement of selected human cells from a heterogeneous population contained on a typical histopathology biopsy slide. The laser microdissection technique is generally described in the published article: Laser Capture Microdissection, Science, Volume 274, Number 5289, Issue 8, pp 998-1001, published in 1996, incorporated herein by reference, and in the following U.S. Pat. Nos. 5,859,699, 5,985,085, 6,184,973, 6,157,446, 6,215,550, 6,459,779, 6,495,195, 6,512,576 and 6,528,248 all herein incorporated by reference in their entirety.

Laser microdissection systems generally comprise an inverted microscope fitted with an infrared laser. Tissue samples are mounted on a standard glass slide and a transparent thermoplastic transfer film is placed over the section. This film is often manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed.

The laser melts the film in precise locations which serves to bind the film to a targeted cell or cells. Individual cells or clusters of cells can be targeted by the laser depending on the diameter of light emitted from the laser. Heat generated by the laser is dissipated by the film, thus limiting the damage done to the targeted cells and the components therein. After the targeted cells are bound to the transfer film, isolation and separation of the targeted cells from the sample occur when the film with the adhered targeted cells are removed from the sample. The targeted cells are then extracted for further analysis. The transfer film can be mounted on a transparent cap that fits on a microcentrifuge tube to facilitate extraction.

The following invention is a new method for laser microdissection that solves a number of problems of conventional laser microdissection and provides the ability to capture moisture-containing samples including live cells from cell cultures. As a practical example, this method allows for colonies of cells grown in slightly modified microtiter plates to be culled using a modified laser microdissection process. The invention also provides a method of capturing cells with improved visualization and a means of minimizing non-specific transfer of unwanted cells without the need for non-contact films or methods designed to space the transfer film from the sample.

BRIEF SUMMARY OF THE INVENTION

In accordance with one aspect of the invention, there is provided laser microdissection method employing a polymer membrane. The method includes the step of providing a first substrate having an upper surface. A polymer membrane having an upper surface and a lower surface is also provided as is a layer of biological material. The biological material is located between the lower surface of the membrane and the upper surface of the first substrate. A second substrate with a transfer film is introduced. The transfer film has adhesive characteristics upon activation by electromagnetic energy. At least one targeted portion of biological material to be microdissected is identified. The second substrate with the transfer film is placed into juxtaposition with the first substrate on the upper side of the membrane in the location of the at least one targeted portion of biological material such that the transfer film is between the second substrate and the membrane. A laser source is provided and activated to emit a laser beam. The laser beam is directed to activate at least a portion of the transfer film and fuse the portion of the transfer film to the membrane. The second substrate with its attached transfer film, a portion of the membrane fused to the transfer film and the at least one targeted portion of biological material adhered to the membrane is separated from the remaining layers of membrane and biological material transferring the targeted biological material to the carrier.

In accordance with another aspect of the invention, there is provided a method for laser microdissection. The method includes the step of providing a first substrate having an upper surface. A polymer membrane having an upper surface and a lower surface is also provided as is a layer of biological material. The biological material is applied to the upper surface of the membrane. The membrane is inverted and placed in contact with the first substrate such that the biological material contacts the upper surface of the first substrate and the upper surface of the membrane faces the upper surface of the first substrate. A second substrate having a surface with a transfer film adhered to the surface is introduced. The transfer film has adhesive characteristics upon activation by electromagnetic energy. At least one targeted portion of biological material to be microdissected is identified. The second substrate with the transfer film is placed into juxtaposition with the first substrate on the side of the membrane in the location of the at least one targeted portion of biological material. A laser source is provided and activated to emit a laser beam. The laser beam is directed so as to describe at least one closed or substantially closed path around the at least one targeted portion of biological material to be microdissected. The laser activates the transfer film and fuses the transfer film to the membrane along the described path defining an interior and exterior of the described path. The second substrate with its attached transfer film, a portion of the membrane fused to the transfer film along the described path, a portion of the membrane interior of the described path and the at least one adhered targeted portion of biological material adhered to the membrane interior of the described path is separated from the remaining layers of membrane and biological material.

In accordance with another aspect of the invention, there is provided a method for laser microdissection. The method includes the step of providing a first substrate having an upper surface. A polymer membrane having an upper surface and a lower surface is also provided as is a layer of biological material. The biological material is applied to the upper surface of the first substrate. The membrane is placed on at least a portion of biological material located on the first substrate. A second substrate having a surface with a transfer film adhered to the surface is introduced. The transfer film has adhesive characteristics upon activation by electromagnetic energy. At least one targeted portion of biological material to be microdissected is identified. The second substrate with the transfer film is placed into juxtaposition with the first substrate on the side of the membrane in the location of the at least one targeted portion of biological material. A laser source is provided and activated to emit a laser beam. The laser beam is directed so as to describe at least one closed or substantially closed path around the at least one targeted portion of biological material to be microdissected. The laser activates the transfer film and fuses the transfer film to the membrane along the described path defining an interior and exterior of the described path. The second substrate with its attached transfer film, a portion of the membrane fused to the transfer film along the described path, a portion of the membrane interior of the described path and the at least one adhered targeted portion of biological material adhered to the membrane interior of the described path is separated from the remaining layers of membrane and biological material.

Figure 1:
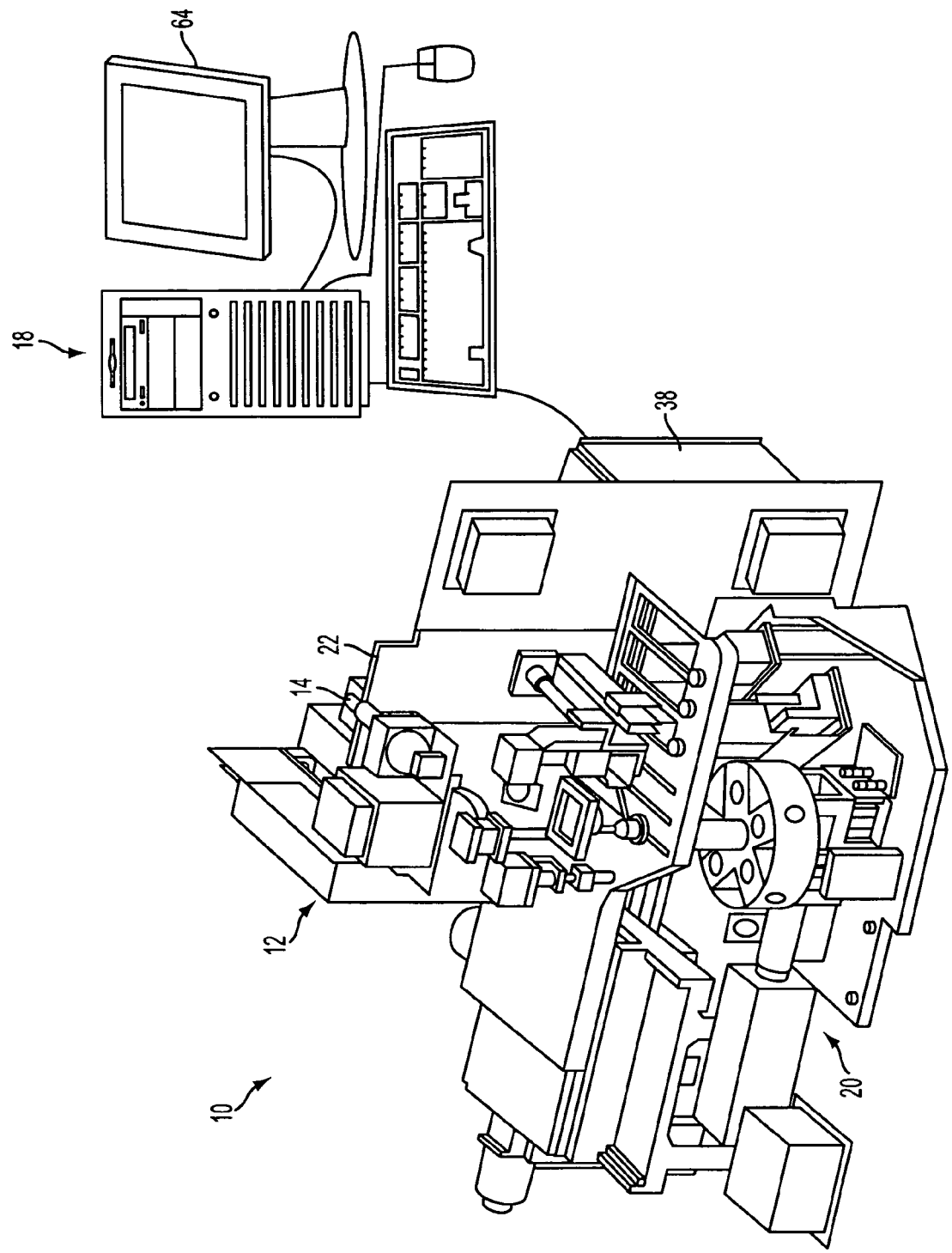
FIG. 1 illustrates a perspective view of an automated laser microdissection device.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DESCRIPTION OF THE INVENTION

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The entire contents of U.S. Provisional Application Ser. No. 60/518,029, entitled "Laser capture microdissection on inverted polymer films," filed on Nov. 7, 2003; U.S. Pat. No. 6,469,779 filed Feb. 4, 1998, entitled "Laser Capture Microdissection Device"; U.S. Pat. No. 5,859,699, filed Feb. 7, 1997 entitled "Laser Capture Microdissection Analysis Vessel"; U.S. Pat. No. 6,495,195, filed Feb. 14, 1997 entitled "Broadband Absorbing Film for Laser Capture Microdissection"; U.S. Pat. No. 6,528,248, filed May 1, 2000 entitled "Processing Technology for LCM Samples"; U.S. Pat. No. 5,985,085, filed Dec. 4, 1997 entitled "Consumable for Laser Capture Microdissection and Method of Manufacture"; U.S. Patent Publication No. 2001-0038449 published Nov. 8, 2001, entitled "Consumable for Laser Capture Microdissection"; U.S. Pat. No. 6,690,470, filed Nov. 6, 2000 entitled "Automated Laser Capture Microdissection"; U.S. Patent Publication No. 2002-0090122, published Jul. 11, 2002 entitled "Road Map Image Guide for Automated Microdissection"; and U.S. Patent Publication No. 2004-0093166, published May 13, 2004 entitled "Interactive and Automated Tissue Image Analysis with Global Training Database and Variable Abstraction Processing in Cytological Specimen Classification and Laser Capture Microdissection Applications" are all hereby expressly incorporated by reference into the present application as if fully set forth herein.

APPARATUS

A laser microdissection device operates to carry out the following general steps. A tissue or smear fixed on a standard microscope slide by routine protocols is introduced into a laser microdissection instrument. A transfer film is provided which is typically affixed to a solid substrate forming a carrier. The carrier can be of any shape. One shape for the carrier is a cap for conveniently introducing a sample into a vessel, such as a microcentrifuge tube, and sealing the vessel. The words "cap" and "carrier" are used interchangeably and it is understood by one skilled in the art that the carrier can be of any shape even where the term "cap" is employed.

The tissue sample mounted on a substrate surface is placed adjacent a transfer film carrier cap which further ensures that transfer film stays out of contact with the tissue at this stage. Alternatively, the transfer film carrier can be brought into contact with the tissue. Upon visualizing the tissue by a microscope, a user may select a region for microdissection. The selected section of the tissue is captured by pulsing at least one region of the transfer film with a low power infrared laser which activates the transfer film which then expands into contact with the tissue. The at least one activated region of the transfer film adheres to the at least one identified portion of desired cell(s) of the tissue sample. Microdissection is completed by lifting the transfer film carrier, with the desired cell(s) attached to the film surface while the surrounding tissue remains intact. Extraction and subsequent molecular analysis of the cell contents, DNA, RNA or protein, are then carried out by standard methods.

Laser microdissection employs a polymer transfer film that is placed on top of the tissue sample. The transfer film may or may not contact the tissue sample. This transfer film is typically a thermoplastic containing organic dyes that are chosen to selectively absorb in the near infrared region of the spectrum overlapping the emission region of common AlGaAs infrared laser diodes. When the film is exposed to the focused laser beam the exposed region is heated by the laser and melts, adhering to the tissue in the region that was exposed. The transfer film exhibits adhesive characteristics upon activation by electromagnetic energy. The film is then lifted from the tissue and the selected portion of the tissue is removed with the film. Thermoplastic transfer films such as a 100 micron thick ethyl vinyl acetate (EVA) film available from Electroseal Corporation of Pompton Lakes, N.J. (type E540) have been used in LCM applications. The film is chosen due to its low melting point of about 90° C.

A laser microdissection instrument 10 generally comprises a microscope 12, an infra-red (IR) laser source 14, and a computer 18 as shown in FIG. 1. The IR laser source 14 and microscope 12 are connected to the computer 18. The instrument 10 may also include a fluorescence system 20. The computer 18 receives input and controls the operation of the microscope 12, laser 14 and fluorescence system 20.

Figure 2:
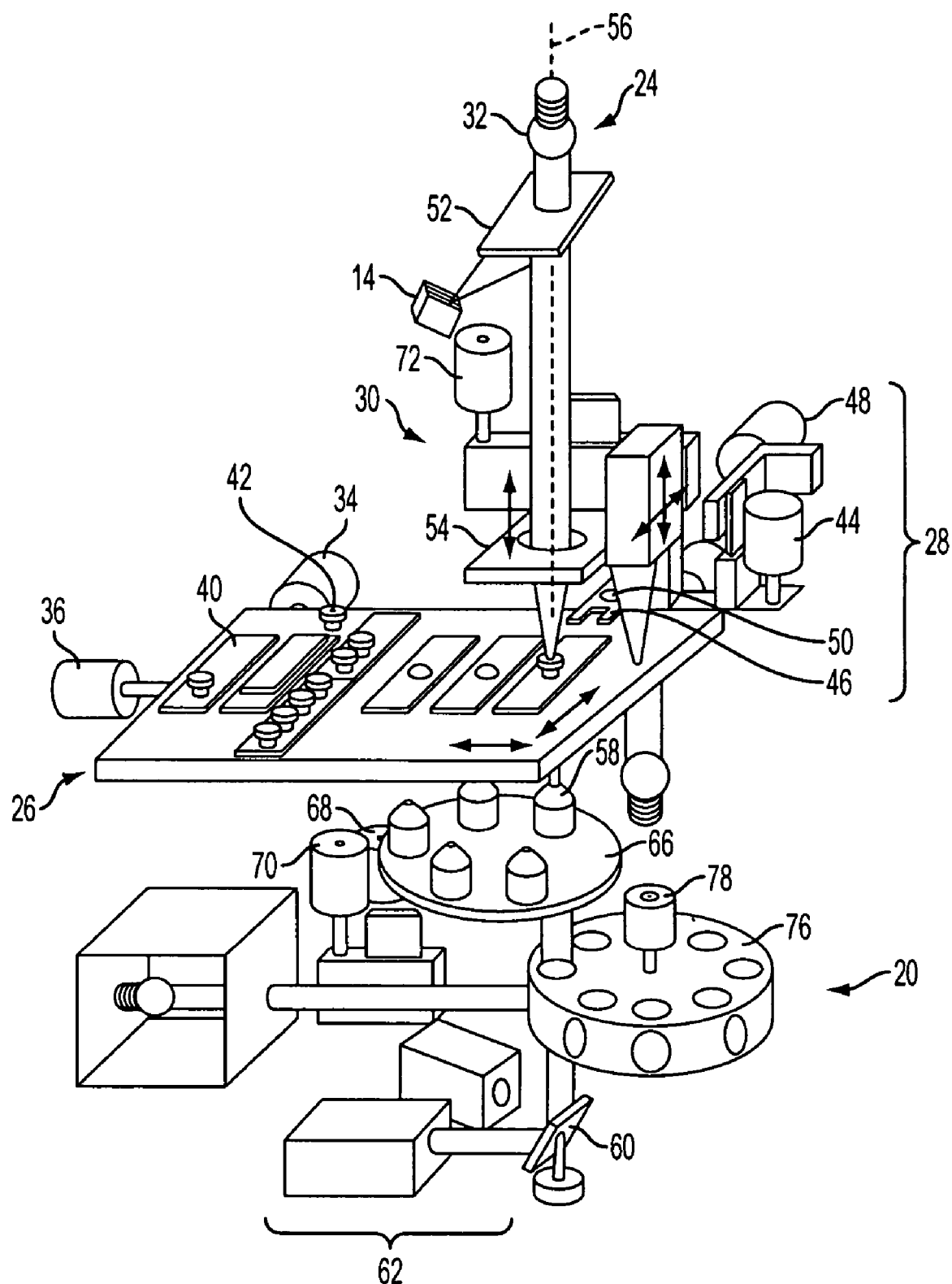
FIG. 2 illustrates a top level block diagram of the components of an automated laser microdissection device.

The microscope 12 includes an arm 22, an illumination system 24, a translation stage 26, a handling system 28 and an optical system 30 as shown in FIG. 2. The microscope arm 22 serves as a frame for carrying the components of the microscope. The illumination system 24 comprises a white light illuminator 32 such as a condenser lamp mounted on the arm. The illumination system 24, translation stage 26 and optical system 30 are arranged in an inverted transmitted-light microscope fashion such that the illumination system is arranged above the translation stage and at least one objective is arranged below the translation stage.

The translation stage 26 is also mounted on the microscope arm 22 and is adapted for receiving one or more specimens and transmitting light therethrough. A vacuum chuck may also be included to secure the specimen mounted on a specimen holder. The translation stage is automatically or manually movable in all directions, in particular, the planar X-Y directions. The automated translation stage includes a lateral translation motor 34 and a fore-and-aft translation motor 36 to allow complete manipulation in the X-Y plane. The motors are controlled by a controller 38 connected to the computer which receives input such as via a mouse cursor. A mouse cursor can be used by an operator to trace a path on a visual display unit depicting a live or static image of the specimen to effect movement of the translation stage. A sophisticated road-map imaging system for navigating the specimen is described in U.S. Patent Publication No. 2002-0090122 which is incorporated herein by reference in its entirety. The translation stage provides a worksurface for handling multiple tissue samples simultaneously. The worksurface also includes a staging area 40, an output station 42 and a quality control station.

The handling system 28 is connected to the translation stage and comprises a lift fork 46. The lift fork 46 is moved in and out of the work surface by a translation motor 44 and a lift motor 48 operates to move the lift fork vertically. The lift fork is adapted to pick a carrier located at a staging or supply area of the translation stage and place the carrier in juxtaposition with the tissue specimen. When microdissection is completed, the lift fork is adapted to pick the carrier from juxtaposition with the specimen and place it in the output station where the carrier may further cap an analysis vessel. The handling system also includes a visualizer filter 50. The visualizer filter is a piece of diffuser glass positioned above the tissue sample. The light from above is diffused by the visualizer filter illuminating the sample from all angles. The visualizer filter can be moved in and out of position and is located on the lift fork. The automated handling system is described in detail in U.S. Pat. No. 6,690,470 to Baer et al. and is incorporated herein by reference in its entirety.

The optical system 30 of the microscope includes several optical elements known to a person skilled in the art to make a microscope and laser microdissection instrument operate properly. These elements mounted on the microscope arm are combined to create an optical train of optical elements for pathing light. The optical system includes but is not limited to the following optical elements: mirror(s), dichroic mirror(s), lens(es), objective, beam-diameter adjuster, cut-off filter, diffuser, condenser, eyepiece and image acquisition system such as a camera.

The optical system together with its optical elements are arranged such that white light from the illumination system passes down toward the translation stage. The white light passes a condenser (not shown), dichroic mirror 52 and a focusing lens 54. The white light passes through the translation stage along a primary optical axis 56 and enters an objective 58 located beneath the translation stage 26. White light from the objective is then reflected by one or more mirrors to an eyepiece (not shown) and/or an image acquisition system 62. The live image captured by the image acquisition system is transmitted to the computer and displayed on a visual display unit 64. Static images may also be taken by the image acquisition system. A cut-off filter is typically located between the objective and the image acquisition system or eyepiece. A diffuser and a beam diameter adjuster (not shown) may also be incorporated in the optical train and located between the dichroic mirror and the translation stage. A series of microscope objectives may be selectably deployed from an objective turret wheel 66 which is controlled by an objective wheel motor 68 while a second objective focus motor 70 operates to adjust the foci of objectives which have been positioned. One skilled in the art will understand that the optical elements may be arranged in various ways for optimum performance.

Connected to the microscope is an infrared (IR) laser source 14. The IR laser source is typically a AlGaAs laser diode having a wavelength of approximately 810 nanometers. The thermoelectric cooled laser diode with collimating optics emits a beam of IR laser light that is incident upon the dichroic mirror 52. The infrared laser beam enters the optical train at the dichroic mirror and is reflected downward through the focusing lens 54 and/or beam diameter adjuster toward the translation stage. Simultaneously, the dichroic mirror allows white light from the illumination system to also pass toward the translation stage resulting in the IR laser beam and the white light illumination being superimposed along the primary optical axis 56. A laser focus motor 72 which is connected to the controller 38 and computer 18 operates to control the focusing lens and adjust the IR laser beam spot size. The computer also delivers signals to the laser via the controller to initiate IR laser pulses, adjust beam size and control IR laser power.

The IR laser operates in two modes, idle mode and pulse mode. In idle mode, the IR laser beam path provides a visible low amplitude signal that can be detected via the image acquisition system when a visual alignment of the laser spot with a portion of tissue is desired. In pulse mode, the IR laser beam path delivers energy for microdissection and the optical characteristics of a cut-off filter attenuate the IR laser beam path sufficiently such that substantially none of the energy from the IR laser beam exits through the microscope.

Suitable laser pulse widths are from 0 to approximately 1 second, preferably from 0 to approximately 100 milliseconds, more preferably approximately 50 milliseconds. In one variation, the spot size of the laser at the transfer film is variable from 0.1 to 100 microns, from 1 to 60 microns, or from 5 to 30 microns. From the standpoint of the clinical operator, the widest spot size range is the most versatile. A lower end point in the spot size range on the order of 5 microns is useful for transferring single cells.

Suitable lasers can be selected from a wide power range. For example, a 100 watt laser can be used. On the other hand, a 50 mW laser can be used. The laser can be connected to the rest of the optical subsystem with a fiber optical coupling. Smaller spot sizes are obtainable using diffraction limited laser diodes and/or single mode fiber optics. Single mode fiber allows a diffraction limited beam.

While the laser diode can be run in a standard mode such as $TEM_{00}$, other intensity profiles are used for different types of applications. Further, the beam diameter is adjusted with a stepped lens (not shown) placed in the lens assembly. Changing the beam diameter permits the size of the portion of the transfer film that is activated to be adjusted. Given a tightly focused initial condition, the beam size is increased by defocusing. Given a defocused initial condition, the beam size is decreased by focusing. The change in focus can be in predetermined fixed amounts. Alternatively, the change in focus is obtained by means of indents on a movable lens mounting and/or by means of optical glass steps. In any event, increasing or decreasing the optical path length is the effect that is needed to alter the focus of the beam, thereby altering the spot size. For example, inserting a stepped glass prism into the beam so the beam strikes one step thread will change the optical path length and alter the spot size.

Another component connected to the microscope is a fluorescence system 20. The fluorescence system is adapted for automated selection of cells or specific regions of a sample for microdissection using fluorescently-stained tissue samples. In image analysis, the fluorescently-labeled tissue is placed in a microdissection instrument and with the fluorescent system, the cells are detected through an analysis of the image formed by the microscope. Image analysis is known in the art and is also described in detail in U.S. Patent Publication No. 2004-0093166, published May 13, 2004 entitled "Interactive and Automated Tissue Image Analysis with Global Training Database and Variable Abstraction Processing in Cytological Specimen Classification and Laser Capture Microdissection Applications" which is herein incorporated by reference in its entirety.

The fluorescence system 20 includes a fluorescence excitation light source, for example, a xenon or mercury lamp 74, which emits a specific wavelength or wavelength range. The specific wavelength or wavelength range of a beam emitted by the light source is selected by a fluorescence filter wheel 76 operated by a fluorescence filter changer motor, to excite a fluorescent system (chemical markers and optical filtering techniques that are known in the industry) that is incorporated in or applied to the sample to be microdissected. The wavelength range transmitted from the excitation light source can be selected. The sample includes at least one member selected from the group consisting of chromophores and fluorescent dyes (synthetic or organic), and the process of operating the instrument includes identifying at least a portion of the sample with light that excites at least one member, before the step of transferring a portion of the sample to the laser microdissection transfer film. The fluorescent laser beam can be made coincident or coaxial with both the IR laser beam path and the white light from illuminator path. Fluorescence emitted by the sample is amplified by an objective changer 66, reflected by a camera changer mirror and captured for live viewing by the acquisition system which comprises a camera. An objective changer motor and a focus motor operate to adjust the fluorescent laser beam and the emitted fluorescent beam. Optionally the objective changer may be implemented in the form of a wheel to accommodate a multiplicity of objectives (five objectives, as depicted) for providing different amplifications of the fluorescent image for the cameras. A more detailed exposition of automated fluorescent laser microdissection is found in U.S. Pat. No. 6,690,470 filed Nov. 6, 2000 and entitled "Automated Laser Capture Microdissection" which is incorporated herein by reference in its entirety.

METHOD

Figure 3A:
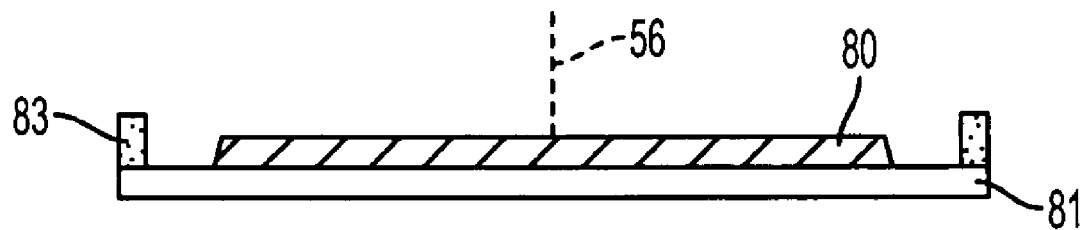
FIG. 3a illustrates a side elevation view of a tissue sample mounted on a polymer membrane connected to a frame according to one variation of the invention.

With reference to FIG. 3a, a sample 80 of biological material to be microdissected is applied to a membrane 81. The membrane 81 is typically a polymer membrane such as a polyester. The polymer membrane is thin enough to maximize the ability to capture small sections and also has enough physical integrity to be handled in the process. The membrane is selected to adhere to the transfer film in the activated region and break away from surrounding non-activated and non-selected regions. The polymer membrane is transparent so that the tissue sample can be visualized through the membrane. Also, the membrane is selected to be compatible with the reagents used in fixing and staining biological tissue. Therefore, depending upon the selected membrane, staining protocols that may compromise lipid, carbohydrate, and other macromolecular targets are avoided. One material suitable for the membrane is polyethylene naphalate (PEN) having a thickness of approximately 1.0 to approximately 2.0 micrometers.

The membrane is typically carried by a frame 83. The frame 83 can be a framed-foil slide such as that described in WO2002/057746A2 which is incorporated herein by reference as if fully set forth herein. A framed-foil slide is simply a frame in the shape of a glass slide with a window such that the membrane is affixed to the frame with the membrane covering the window. A petrie dish with a membrane bottom and firm side walls (glass, metal or plastic such as polystyrene or polycarbonate) works well too. The small cavity formed by the side walls of the window of the framed slide or the petrie dish provides some depth for growing cells and adding growth medium. Various coatings such as poly-1-lysine and growth media can be added to the petrie dish or framed slide to assist in cell viability and growth. The petrie dish or framed slide can be covered with an appropriate top to provide for isolation.

The sample 80 of biological material can be prepared in all of the standard means including sectioning by microtome, smears and cytospins. The sample can also be prepared by growing cells onto the polymer membrane film in order to harvest live cells. The tissue or cells are attached directly to the membrane layer. Tissue preparation protocols that result in strong adhesion to the polymer membrane and which also allow for the microdissection of hydrated samples and live cell samples are used. Tissue preparation protocols are followed in order to assure that the tissue adheres enough to survive the liquid processing, but that the adhesion is weak enough to allow microdissection to occur. If the capture of hydrated living cells is not desired, the tissue sample is typically exposed to ethanol with diminishing levels of water and finally exposed to xylene. A cryostat is employed for cutting sections of frozen tissue in which a microtome is contained within a refrigerated chamber having a temperature maintained at a preset level. The room-temperature framed PEN slide, for example, is introduced into the cryostat and the cut frozen section adheres to the room temperature framed PEN membrane. Afterwards, the slide is treated as a regular frozen section ready for microdisseciton. In another variation, a paraffin section is placed onto the framed PEN membrane and then treated as a slide ready for laser microdissection.

Figure 3B:
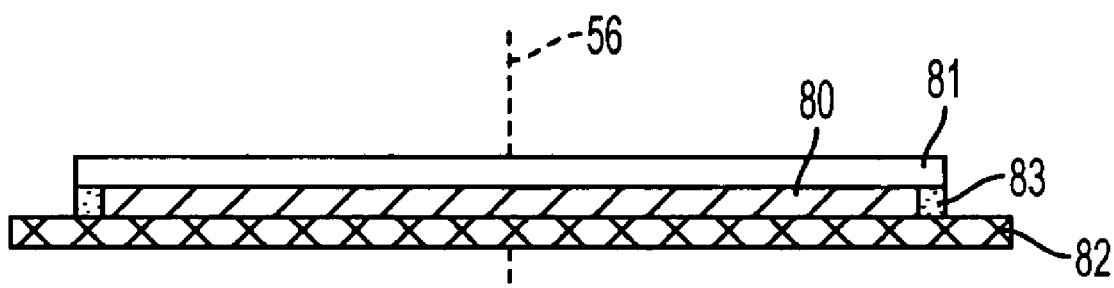
FIG. 3b illustrates a side elevation view of a tissue sample mounted on a polymer membrane connected to a frame and inverted onto a substrate according to one variation of the invention.
Figure 3C:
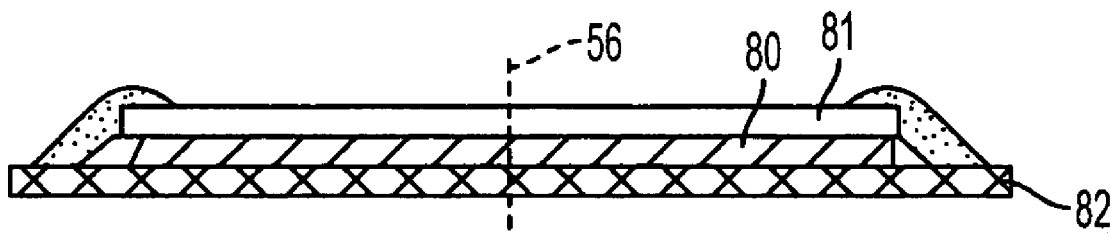
FIG. 3c illustrates a side elevation view of a tissue sample located between a polymer membrane and substrate according to one variation of the invention.

The membrane 81 with the sample 80 of living or non-living tissue mounted on its upper surface is inverted and placed in contact with a substrate 82 such that the biological material 80 contacts the upper surface of the substrate 82 and the upper surface of the membrane faces the upper surface of the substrate 82 as shown in FIG. 3b. If live cells are used, most of the growth medium is removed. The substrate is typically a glass slide. If a frame 83 is not being using, the polymer membrane 81 is adhered to the substrate 82 as shown in FIG. 3c. The layer of biological material 80 is located between the membrane and the substrate. The substrate, membrane and sample are inserted into the laser microdissection instrument, positioned in the optical axis 56 and imaged.

Alternatively, the sample 80 of living or non-living tissue is directly mounted on the upper surface of the substrate 82 instead of directly mounted or grown on the membrane 81. The sample 80 is prepared on the substrate 82 which is typically a glass slide such that the sample 80 releases from the slide easily in order to become captured. Tissue preparation protocols are followed in order to assure that the tissue adheres sufficiently to the substrate to survive the liquid processing, but that the adhesion is sufficiently weak to allow microdissection to occur. The membrane 81 is overlayed onto the sample 80 as shown in FIG. 3c. Hence, the layer of biological material 80 is located between the membrane and the substrate. The substrate, membrane and sample are inserted into the laser microdissection instrument, positioned in the optical axis 56 and imaged.

Figure 3D:
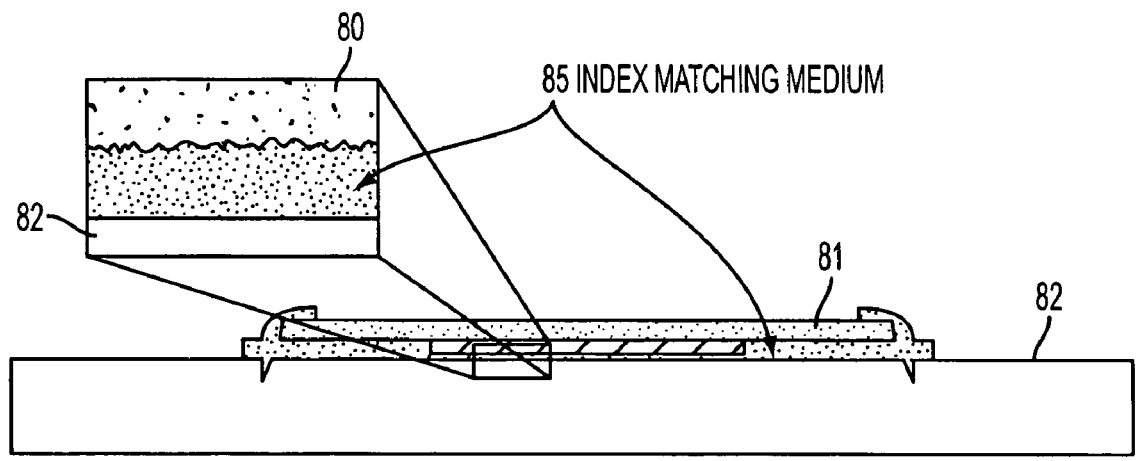
FIG. 3d illustrates a side elevation view of a tissue sample and index-matching medium located between a polymer membrane and substrate according to one variation of the invention.

In another variation, with either case mentioned above, whether the sample 80 is mounted on a membrane 81 and then inverted or whether the sample 80 is mounted on a substrate 82 and then overlayed with a membrane, an index-matching medium 85 is employed. By providing an index-matching medium 85 between the membrane 81 and the substrate 82, the scattering of light at the tissue-air interface is significantly reduced. The tissue-air interface is typically formed between the sample 80 and substrate 82 when the sample is mounted on the membrane 81 and then inverted as shown in FIG. 3d. When the sample is mounted on the substrate 82, the tissue-air interface is typically formed between the sample 80 and the membrane 81. In either case, the index-matching medium 85 is provided to substantially fill the tissue-air interface. The index-matching medium 85 does not impede microdissection and results is greatly improved visualization. The index-matching medium 85 is a liquid or solid. If it is a solid, it is desirable that it be physically weak such as a gel. The medium can be aqueous or organic. Some choices for an index-matching medium 85 are water, ethanol, xylene, gelatin, and mineral oil.

With the substrate, membrane and sample inserted into the laser microdissection instrument and positioned in the optical axis 56, the handling system 28, in particular the lift fork 46, is used to bring a carrier 84 with a transfer film 86 affixed to its surface also into the optical axis 56 and in juxtaposition with the substrate 82 on the side of the membrane 81. In one variation, the carrier is placed in contact with the membrane 81 such that the transfer film 86 contacts the membrane substantially across the entirety of the transfer film surface as shown in FIG. 3e. The transfer film 86 does not come into contact with the biological sample 80. Instead, the transfer film 86 contacts the membrane 81 which serves as a barrier layer that prevents the transfer of undesired tissue fragments and other particles normally adherent to the sample section. Hence, the membrane 81 reduces the need for employing non-contact laser microdissection methods that avoid non-specific transfer of friable tissue matter and other particles.

Figure 3F:
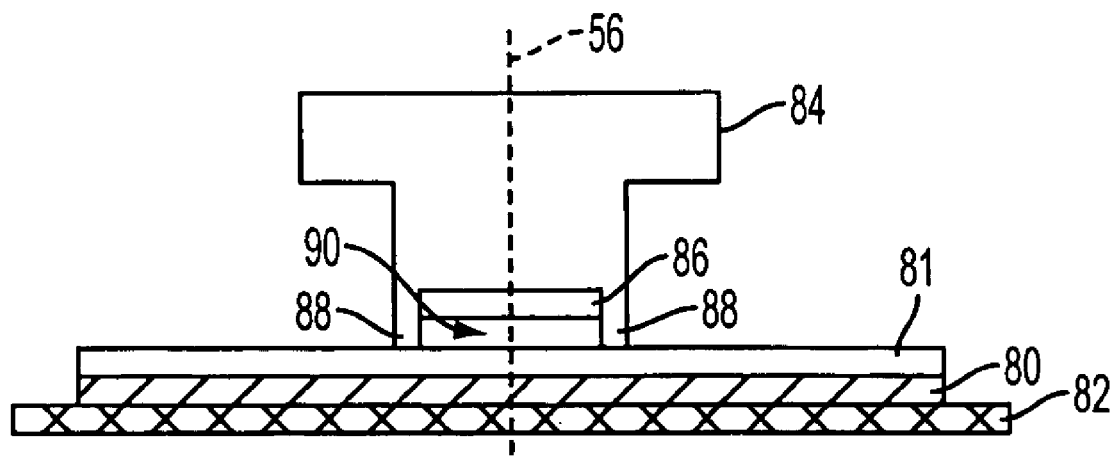
FIG. 3f illustrates a side elevation view of a transfer film carrier with standoffs in juxtaposition with a polymer membrane according to one variation of the invention.
Figure 3E:
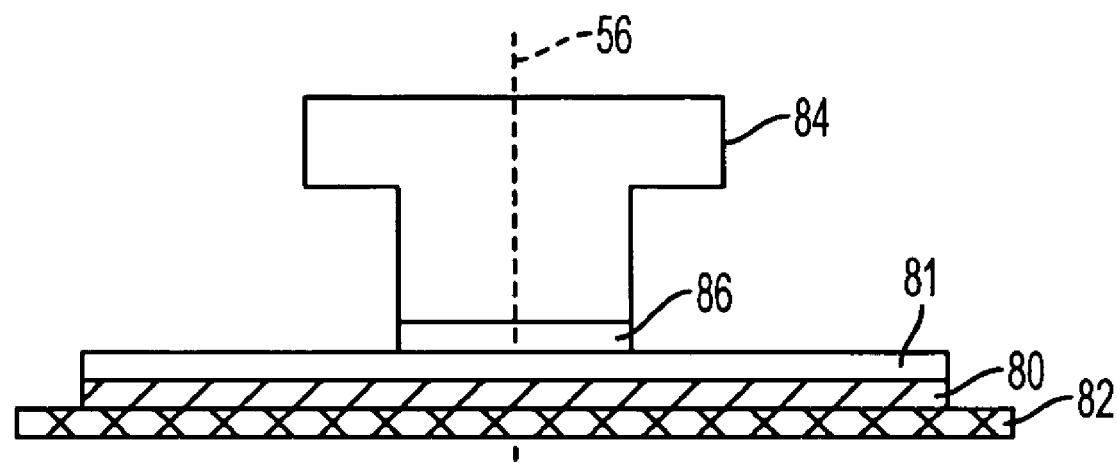
FIG. 3e illustrates a side elevation view of a transfer film carrier in juxtaposition with a polymer membrane according to one variation of the invention

Alternatively, as shown in FIG. 3f, the transfer film 86 is spaced apart from the membrane. In one variation, the carrier is formed with standoffs 88 such that a substantial portion of the transfer film 86 does not contact the membrane 81 but remains spaced from the membrane 81 by a distance 90 sufficient for promoting adhesion of the transfer film to the membrane upon activation of the transfer film by the laser. Standoffs are described in U.S. Patent Publication No. 2001-0038449 published Nov. 8, 2001, entitled "Consumable for Laser Capture Microdissection" which is herein incorporated by reference in its entirety. Standoffs are structural features that protrude from the surface of the carrier on the side of the transfer film to provide a spacing between the transfer film and the membrane in order to avoid transfer of unwanted material that would otherwise adhere to the transfer film due to electrostatic forces and the like.

With the sample in the optical axis, the illumination system 24 is activated shedding light on the sample. The white light penetrating the sample arrives at the objective and is directed to the acquisition system and/or eyepiece. A live image that is captured by the acquisition system is displayed on the computer monitor. Also, a static image of relatively lower magnification is captured so as to provide a roadmap image for navigating the sample space. The two images are displayed side-by-side to locate the user on the sample space map and simultaneously provide a display of the local sample space having a relatively larger magnification. The operator inspects the sample by moving the translation stage via computer inputs, controllers and appropriate software. For example, navigation of the sample space is accomplished by tracing a path on the displayed monitor image using an input cursor via a mouse, joystick or other input means.

Figure 4A:
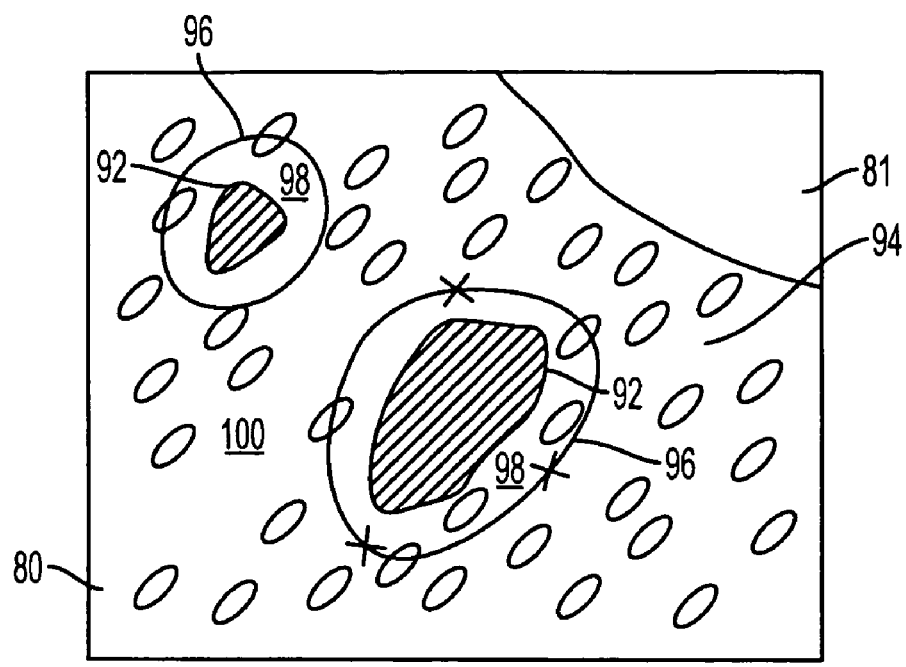
FIG. 4a illustrates a top planar sectional view of a polymer membrane and biological sample with targeted portions encompassed by traces according to the invention.

FIG. 4a illustrates a top planar sectional view of the membrane 81 and biological sample 80 with the membrane 81 shown sectioned away from the sample 80 to uncover detail for descriptive purposes. A targeted portion 92 of biological material 94 is identified for microdissection either manually by the operator or automatically employing software for algorithmic identification of regions of interest. Typically, fluorescent systems are employed for assisting the automated identification of targeted portions of biological material. Manually, the user can trace a targeted portion 92 of biological material viewed on the display monitor by moving a mouse cursor. Alternatively, the trace is performed automatically by the computer with appropriate governing software. Each trace 96 defines an interior 98 and an exterior 100. The interior 98 includes the targeted portion(s) and the exterior 100 of the trace includes non-targeted biological material. One or more targeted portions of biological material can be traced and the trace can be of any shape and size as shown in FIG. 4a.

Figure 4B:
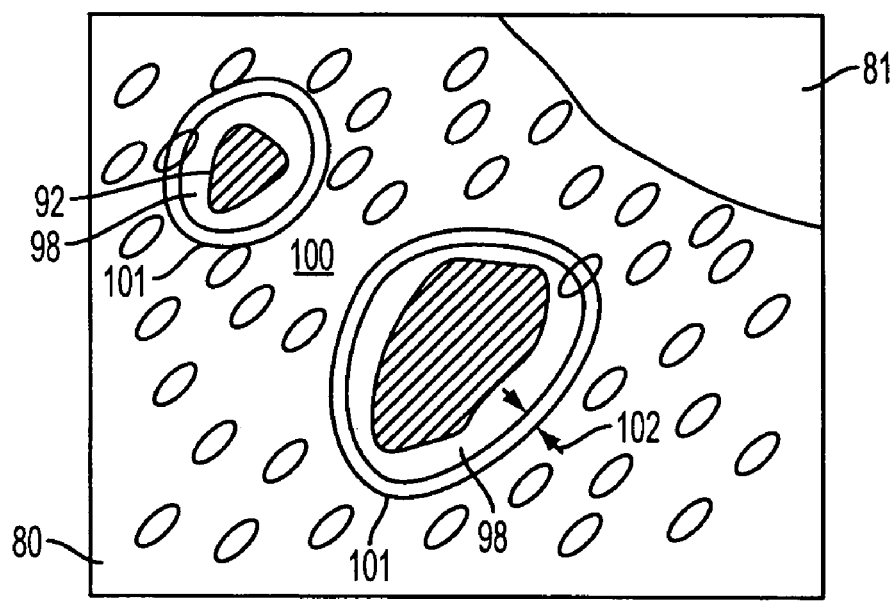
FIG. 4b illustrates a top planar sectional view of a polymer membrane and biological sample with targeted portions encompassed by IR laser beam cut paths according to the invention.

The trace defines a cut line for the IR laser source. After all of the targeted portions 92 have been traced the user is prompted by the computer to commence cutting along the traces with the IR laser source. The user may select whether each of the traces are to be closed or substantially closed paths for the IR laser. If the user selects closed paths, the IR laser source is automatically directed and activated to emit a laser beam to cut along the traces at a predefined cut width 102 forming a cut path 101 that is a complete curve surrounding the cells of interest as shown in FIG. 4b. The IR laser beam activates the transfer film and fuses it to the membrane along the cut path.

Figure 4C:
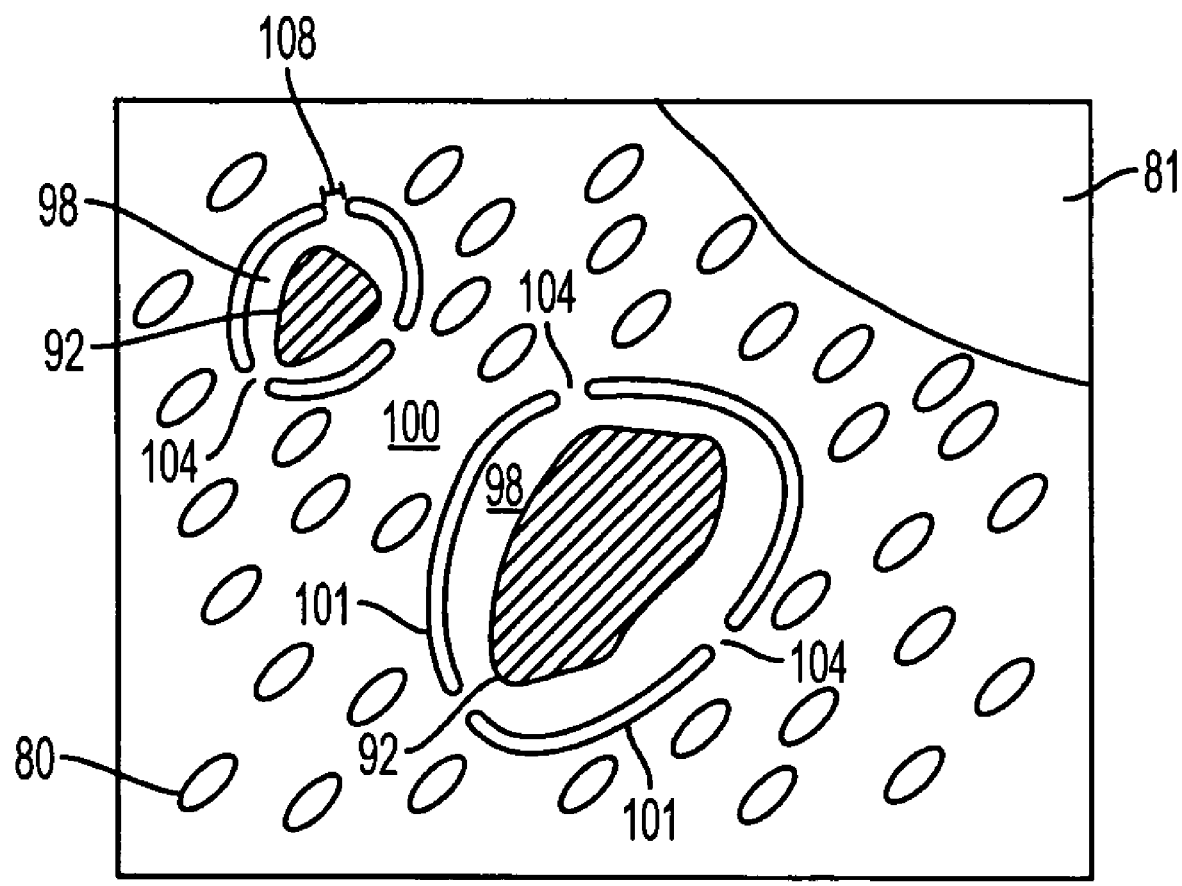
FIG. 4c illustrates a top planar sectional view of a polymer membrane and biological sample with targeted portions encompassed by cut paths that are interspersed with bridges according to the invention.

If the user selects a substantially closed path, at least one bridge 104 spanning from the interior 98 to the exterior 100 will be formed such that the interior 98 is joined to the surrounding exterior 100 at the location of the bridge 104 as shown in FIG. 4c. The cut path 101 is interspersed with bridges 104 formed when the IR laser beam is temporarily de-activated while moving along a trace. The bridge width 108 can be selected by the user or predetermined by controlling software. Bridge locations may be user-defined by clicking with the mouse cursor along the trace at locations where bridges are desired as shown by the "x" in FIG. 4a. The user thereby manually selects any number and location of the bridges. Alternatively, the computer may automatically form a predefined number of bridges. The IR laser is activated which activates the transfer film and fuses it to the membrane along the cut path, but at bridge locations, the membrane remains intact.

During the cutting operation of the IR laser, the laser beam remains stationary and the translation stage serves as a cut line control unit and generates, during the cutting operation, a relative movement between the laser beam and the sample. Alternatively, the cut line control unit comprises a laser scanning device which moves the laser beam relative to the stationary sample during cutting. In such an operation, the translation stage and the sample is not displaced during cutting but remains fixed in the optical axis. The cut line results exclusively from deflection of the laser beam over the sample. In either case, during the cutting operation the IR laser is typically pulsed repeatedly at quick succession along the cut path. Alternatively, the IR laser is fired at duration to completely trace the cut path. The presence of the membrane 81 advantageously diminishes raising the temperature of desired biological material in the proximate area of the IR laser shot which would result from localized heating. The desired cells are not harmed by the IR laser shots.

If a carrier with standoffs is being employed, the transfer film carrier remains in a fixed position relative to the membrane. With the carrier remaining fixed, the transfer film is brought into contact with the membrane when activated. The activated transfer film spans the distance 90 of FIG. 3f of the standoffs 88 to contact and adhere to the membrane 81 along the cut path.

Figure 5:
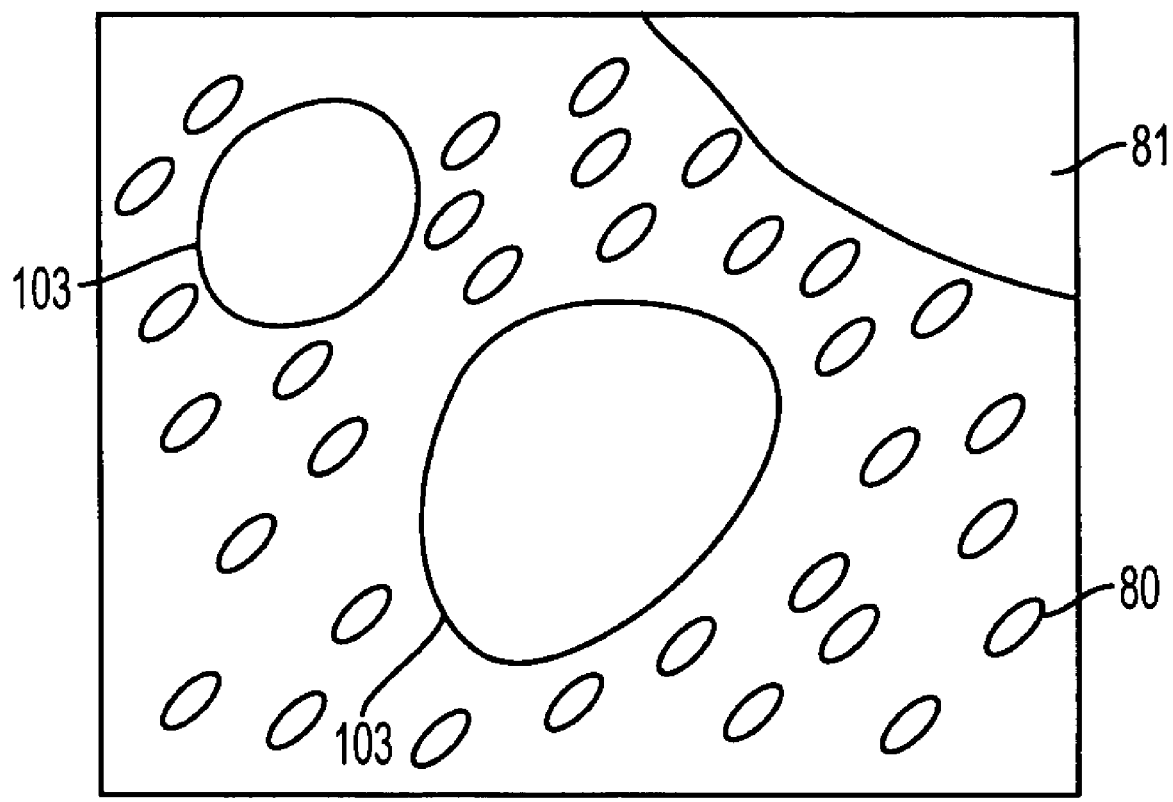
FIG. 5 illustrates a top planar sectional view of a polymer membrane and biological sample with targeted portions removed from the remaining biological material according to the invention.

The carrier with the transfer film will result in one or more areas of adhesion with the membrane located along the IR laser cut path(s). Isolation and separation of the selected cells from the sample occur when the carrier is removed. When the carrier is separated from the membrane by lifting it vertically, the carrier with its attached transfer film and at least one adhered portion of membrane along with targeted portion of biological material is removed from the remaining layers of membrane and biological material. Separating the carrier with its attached transfer film, a portion of the membrane that is fused to the transfer film along the described path includes separating a portion of the membrane interior of the described path and the at least one adhered targeted portion of biological material adhered to the membrane interior of the described path along with the carrier and from the remaining layer of membrane and layer of biological material. If bridges were formed, those bridges are mechanically broken upon lifting the carrier to free the adhered portions of targeted biological material and to transfer them to the carrier. The bond between the fused sections of the transfer film and membrane is so strong that the membrane rips surrounding these sections as shown in FIG. 5. In this manner, the fused sections of membrane and associated cells which are adhered to the membrane are transferred to the carrier. The associated cells are adhered to the membrane by the various living or non-living tissue preparation protocols. What remains is un-targeted biological material and gaps where targeted tissue 103 has been removed as shown in FIG. 5. Being adhered to the membrane 81, the targeted biological material is removed with the carrier and available for further processing. After the live cells are isolated via laser microdissection, they can be extracted for DNA/RNA/protein or recultured. If recultured, the live cells are trypsinized off the laser microdissection carrier. Trypsinization breaks the adhering bonds that help bind the living cells to the membrane releasing the living cells into solution.

Figure 6A:
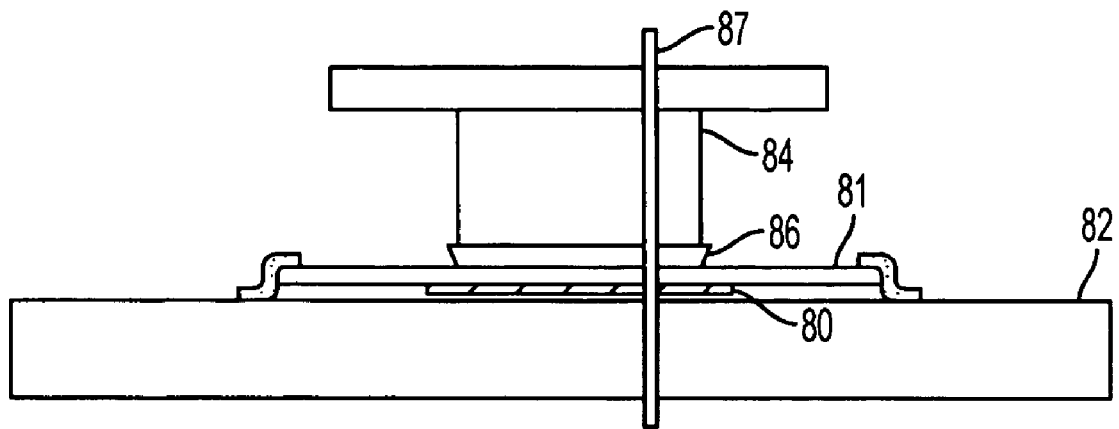
FIG. 6a illustrates a side elevation view of a transfer film carrier, transfer film, polymer membrane, biological material, substrate and laser beam fired directly at targeted portions of biological material according to the invention.
Figure 6B:
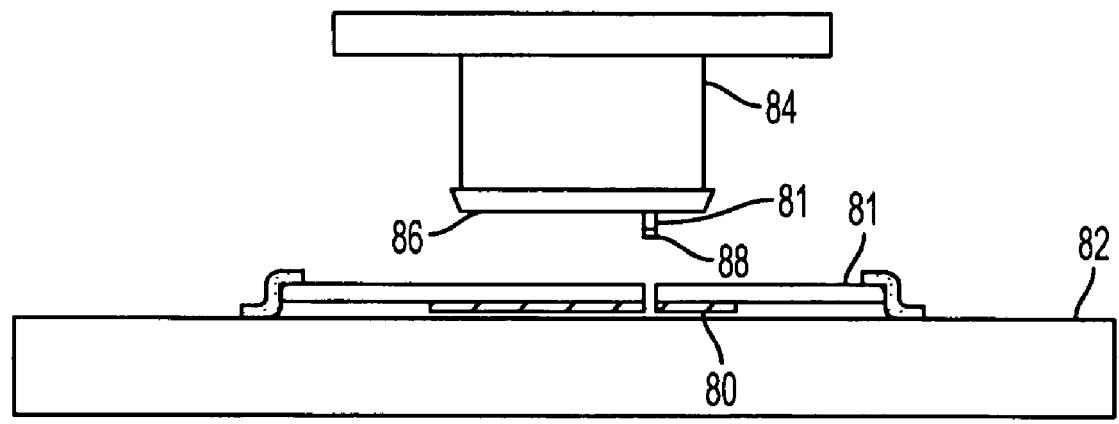
FIG. 6b illustrates a side elevation view of a transfer film carrier, transfer film, fused polymer membrane and an adhered targeted portion of biological material separated from the remaining layers of polymer membrane and biological material according to the invention.

In another variation, the carrier 84 with the transfer film 86 affixed to its surface is positioned in the optical axis 56 and in juxtaposition with the substrate 82 on the side of the membrane 81 either in contact with the membrane 81 as shown in FIG. 3e or spaced from the membrane 81 by a distance sufficient for promoting adhesion of the transfer film to the membrane upon activation of the transfer film as shown in FIG. 3f. After the sample is imaged and the target cell or cells are identified, the IR laser is activated to produce a laser beam which is directed to activate at least a portion of the transfer film and fuse the portion of the activated transfer film to the membrane directly in the location of the targeted cell or cells instead of surrounding the targeted cells with a cut path as described above. FIG. 6a illustrates a carrier 84 in contact with the membrane 81 and an IR laser beam 87 pulsed in a location of targeted cells. The IR laser beam 87 activates the transfer film 86 in the location of the targeted cells fusing the transfer film 86 to the membrane 81 in the location of the targeted cells. Isolation and separation of the targeted cells from the sample 80 occur when the carrier 84 is removed as shown in FIG. 6b. When the carrier 84 is separated from the membrane 81 by lifting it vertically, the carrier 84 with its attached transfer film and at least one adhered portion of membrane together with a targeted portion of biological material 88 is removed from the remaining layers of membrane 81 and biological material 80. The bond between the fused sections of the transfer film 86 and the membrane 81 in the area where the IR laser was activated is so strong that the membrane 81 rips surrounding these sections as shown in FIG. 6b. In this manner, the fused sections of membrane 81 and associated cells 88 are transported to the carrier 84. What remains is un-targeted biological material.

The fused sections can be as large or small as desired and the IR laser can be focused and de-focused to adjust the beam diameter such that the desired portion of the sample is illuminated by the IR laser and subsequently captured. If the beam diameter is kept constant and the area of desired capture is larger than the IR laser beam diameter, the IR laser can be pulsed repeatedly across an entire area of desired cells.

Figure 6C:
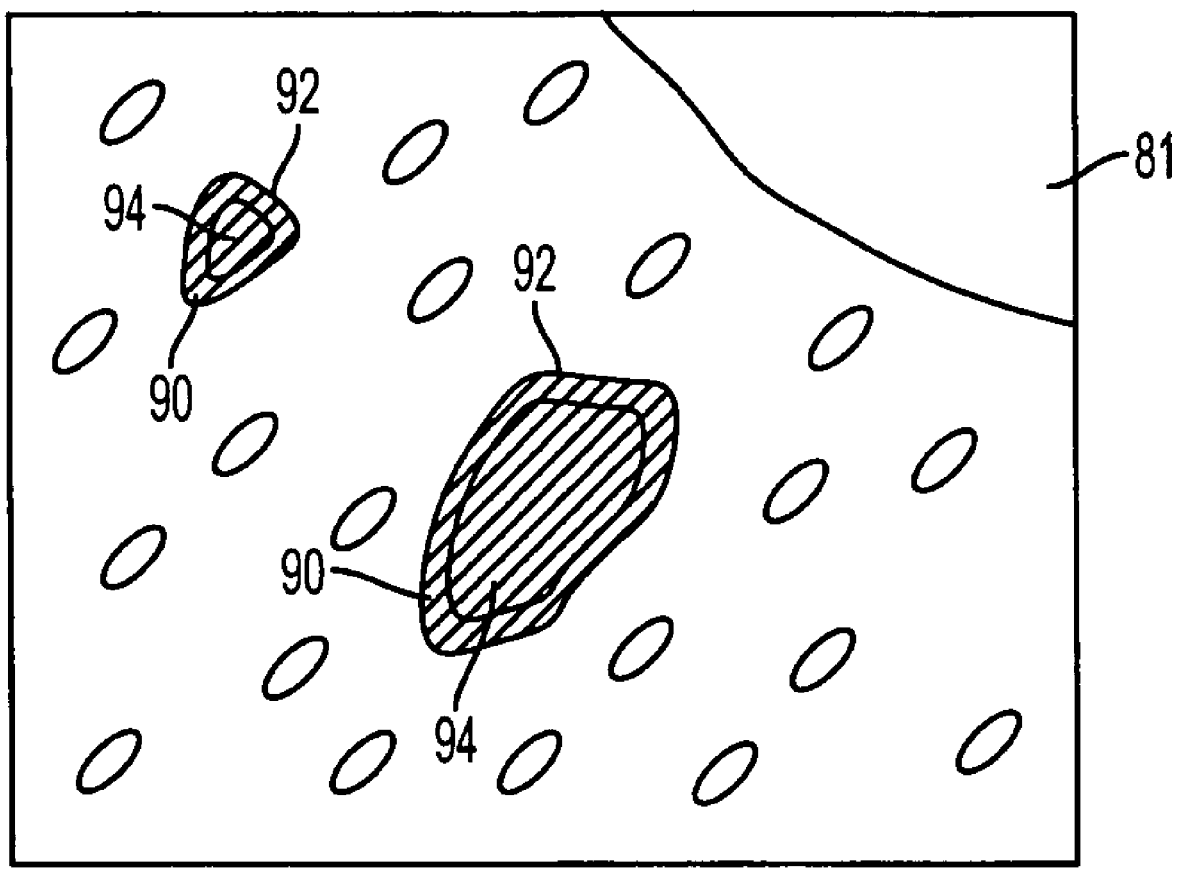
FIG. 6c illustrates a top planar sectional view of a polymer membrane and biological sample with IR laser beam cut paths located along the perimeter of targeted portions of biological material according to the invention.
Figure 6D:
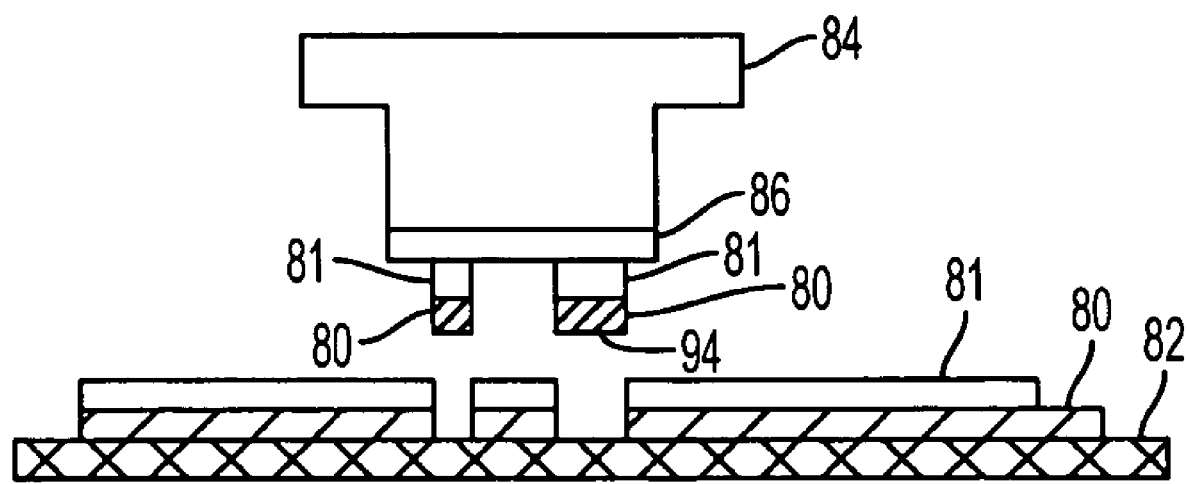
FIG. 6d illustrates a side elevation view of a transfer film carrier with targeted portions adhered thereto and separated from the remaining tissue sample according to the present invention.

In another variation as shown in FIG. 6c, if the area of desired cells 94 is larger than the beam diameter, the IR laser beam is activated along a cut path 90 on the perimeter 92 of the desired cells 94 such that when fused, the membrane 81 rips surrounding the desired cells 94. In this manner, the fused sections of membrane 81 and associated cells are transported to the carrier 84 including the tissue interior of the cut path. What remains is un-targeted biological material as shown in FIG. 5 and FIG. 6d. Being adhered to the membrane, the targeted biological material 94 is removed with the carrier and available for further processing.

EXAMPLE

This example illustrates a precise, rapid and convenient laser capture microdissection method for positive selection of living adherent cells and successful subsequent re-cultivation of homogeneous populations. Human breast cancer (SKBR3) cells were seeded onto a membrane frame slide with 1 mL of SKBR3 cell culture medium and then incubated at 37° C. for four days with 5% carbon dioxide. Fresh medium was added as needed. The medium was aspirated and the back of the membrane slide was wiped with 100% ethanol to remove any moisture. Laser microdissection was performed according to one of the methods described above using the PixCell IIe and AutoPix laser microdissection systems produced by Arcturus Bioscience, Inc. of Mountain View, Calif. The carrier was removed from the slide retaining the selected live cells on the transfer film. 10 μL of Hanks Balanced Saline Solution of Invitrogen Corporation, Carlsbad, Calif., was pipetted onto the cells and incubated for 10 minutes at room temperature and then removed. 10 μL of Trypsin-EDTA (0.25% Trypsin, 1 mM EDTA) was pipetted directly onto the captured cells on the carrier and incubated on the carrier for two minutes at room temperature. Using a 1000 μL pipette tip, the Trypsin/cells were transferred into the well of a sterile 96-well flat-bottomed plate with 50 μL of SKBR3 medium and the plate was placed in the 37° C., 5% carbon dioxide incubator. Within twelve hours, cells attached to the well bottom. Within 24 hours, cell division could be observed.

All publications and patent applications mentioned in this specification are incorporated herein by reference to the same extent as if each individual publication or patent application were specifically and individually indicated to be incorporated by reference.

The above description is illustrative and not restrictive. Many variations will be apparent to those skilled in the art upon review of this disclosure. The scope of the invention should not be determined with reference to the above description, but instead should be determined with reference to the appended claims and the full scope of their equivalents.

What is claimed is:

1. A method for laser microdissection comprising the steps of:
    providing a first substrate having an upper surface;
    providing a membrane having an upper surface and a lower surface;
    providing a layer of biological material;
    locating the layer of biological material between the lower surface of the membrane and the upper surface of the first substrate;
    providing a second substrate having a surface with a transfer film adhered thereto;
    the transfer film having adhesive characteristics upon activation by electromagnetic energy;
    identifying at least one targeted portion of biological material to be microdissected;
    placing the second substrate with the transfer film into juxtaposition with the first substrate on the upper side of the membrane in the location of the at least one targeted portion of biological material such that the transfer film is between the second substrate and the membrane;
    providing a laser source;
    activating the laser source to emit a laser beam;
    directing the laser beam so as to activate at least a portion of the transfer film and fuse the portion of the transfer film to the membrane; and
    separating the second substrate with its attached transfer film, a portion of the membrane fused to the transfer film and the at least one targeted portion of biological material adhered to the membrane from the remaining layers of membrane and biological material.

2. The method of claim 1 wherein the step of directing the laser beam includes directing the laser beam so as to describe at least one closed or substantially closed path around the at least one targeted portion of biological material to be microdissected; the laser beam activating the transfer film and fusing the transfer film to the membrane along the described path and defining an interior and exterior of the described path.

3. The method of claim 2 wherein the step of separating the second substrate includes separating the second substrate with its attached transfer film, a portion of the membrane fused to the transfer film along the described path, a portion of the membrane interior of the described path and the at least one adhered targeted portion of biological material adhered to the membrane interior of the described path from the remaining layers of membrane and biological material.

4. The method of claim 2 wherein the step of directing the laser beam includes describing a substantially closed path such that there remains at least one bridge between the interior and the exterior wherein the interior is joined to the surrounding exterior at the least one bridge.

5. The method of claim 4 wherein the step separating the second substrate includes breaking the at least one bridge.

6. The method of claim 1 further including the step of applying the layer of biological material to the upper surface of the first substrate.

7. The method of claim 1 further including the step of applying the layer of biological material to the lower surface of the membrane.

8. The method of claim 7 wherein the step of locating the layer of biological material between the lower surface of the membrane and the upper surface of the first substrate includes the step of inverting the membrane onto the first substrate.

9. The method of claim 1 wherein the step of directing the laser beam so as to activate at least a portion of the transfer film and fuse the portion of the transfer film to the membrane includes directing the laser beam directly at the least one targeted portion of biological material.

10. The method of claim 9 wherein the step of directing the laser beam so as to activate at least a portion of the transfer film and fuse the portion of the transfer film to the membrane includes directing the laser beam across the entire area of the targeted portion of biological material.

11. The method of claim 9 wherein the step of directing the laser beam so as to activate at least a portion of the transfer film and fuse the portion of the transfer film to the membrane includes directing the laser beam at least a portion of the area of the at least one targeted portion of biological material.

12. The method of claim 9 where the step of directing the laser beam so as to activate at least a portion of the transfer film and fuse the portion of the transfer film to the membrane includes directing the laser beam along the perimeter of the area of the at least one targeted portion of biological material.

13. The method of claim 1 wherein the step of activating the laser source includes repeatedly pulsing the laser source.

14. The method of claim 1 wherein the step of providing a layer of biological material includes providing living cells.

15. The method of claim 1 further including the step of providing an index-matching medium between the membrane and the second substrate.

16. The method of claim 1 wherein the step of placing the second substrate with the transfer film into juxtaposition with the first substrate on the upper side of the membrane includes the step of spacing the transfer film away from the membrane by a distance sufficient for promoting adhesion of the transfer film to the membrane upon activation of the transfer film by the laser source.

17. The method of claim 1 wherein the step of placing the second substrate with the transfer film into juxtaposition with the first substrate on the upper side of the membrane includes the step of contacting the transfer film to the membrane.

18. The method of claim 1 wherein the step of providing a laser source includes the step of providing an IR laser source.

19. A method for laser microdissection comprising the steps of:

providing a first substrate having an upper surface;

providing a membrane having an upper surface and a lower surface;

applying a layer of biological material to the upper surface of the membrane;

placing the membrane in contact with the first substrate such that the biological material contacts the upper surface of the first substrate and the upper surface of the membrane faces the upper surface of the first substrate;

providing a second substrate having a surface with a transfer film adhered to the surface;

providing a second substrate having a surface with a transfer film adhered to the surface;

the transfer film having adhesive characteristics upon activation by electromagnetic energy;

identifying at least one targeted portion of biological material to be microdissected;

placing the second substrate with the transfer film into juxtaposition with the first substrate on the side of the membrane in the location of the at least one targeted portion of biological material;

providing a laser source;

activating the laser source to emit a laser beam;

directing the laser beam so as to describe at least one closed or substantially closed path around the at least one targeted portion of biological material to be microdissected;

the laser activating the transfer film and fusing the transfer film to the membrane along the described path and defining an interior and exterior of the described path; and separating the second substrate with its attached transfer film, a portion of the membrane fused to the transfer film along the described path, a portion of the membrane interior of the described path and the at least one adhered targeted portion of biological material adhered to the membrane interior of the described path from the remaining layers of membrane and biological material.

20. The method of claim 19 wherein the laser source is a IR laser source.

21. The method of claim 19 wherein the step of activating the laser source includes describing a substantially closed path such that there remains at least one bridge between the interior and the exterior wherein the interior is joined to the surrounding exterior at the at least one bridge.

22. The method of claim 21 wherein the step of separating the second substrate includes the step of breaking the at least one bridge.

23. The method of claim 19 wherein the step of placing the second substrate with the transfer film into juxtaposition with the first substrate on the side of the membrane in the location of the at least one targeted portion of biological material includes contacting the transfer film to the membrane.

24. The method of claim 19 wherein the step of placing the second substrate with the transfer film into juxtaposition with the first substrate on the side of the membrane in the location of the at least one targeted portion of biological material includes spacing at least a portion of the transfer film away from the membrane by a distance sufficient for promoting adhesion of the transfer film to the membrane upon activation of the transfer film by the laser source.

25. The method of claim 19 wherein the step of applying a layer of biological material to the upper surface of the membrane includes growing living cells on the upper surface of the membrane.

26. The method of claim 19 further including the step of providing an index-matching medium between the membrane and the second substrate.

27. A method for laser microdissection comprising the steps of:

providing a first substrate having an upper surface;

providing a membrane having an upper surface and a lower surface;

applying a layer of biological material to the upper surface of the first substrate;

placing the membrane on at least a portion of biological material located on the first substrate;

providing a second substrate having a surface with a transfer film adhered to the surface;

the transfer film having adhesive characteristics upon activation by electromagnetic energy;

identifying at least one targeted portion of biological material to be microdissected;

placing the second substrate with the transfer film into juxtaposition with the first substrate on the side of the membrane in the location of the at least one targeted portion of biological material;

providing a laser source;
activating the laser source to emit a laser beam;
directing the laser beam so as to describe at least one closed or substantially closed path around the at least one targeted portion of biological material to be microdissected;
the laser activating the transfer film and fusing the transfer film to the membrane along the described path and defining an interior and exterior of the described path;

separating the second substrate with its attached transfer film, a portion of the membrane fused to the transfer film along the described path, a portion of the membrane interior of the described path and the at least one adhered targeted portion of biological material adhered to the membrane interior of the described path from the remaining layers of membrane and biological material.

* * * * *

UNITED STATES PATENT AND TRADEMARK OFFICE
CERTIFICATE OF CORRECTION

| | |
|---|---|
| PATENT NO. | : 7,456,938 B2 |
| APPLICATION NO. | : 10/982230 |
| DATED | : November 25, 2008 |
| INVENTOR(S) | : Ashi Malekafzali |

It is certified that error appears in the above-identified patent and that said Letters Patent is hereby corrected as shown below:

Title Page item 56 Column 2, Line 2 – Delete "Bio Techiques" and insert -- Bio Techniques --, therefore.

Column 15, Line 57-58 – In Claim 19, after "surface;" delete "providing a second substrate having a surface with a transfer film adhered to the surface;".

Signed and Sealed this

Twenty-eighth Day of April, 2009

JOHN DOLL
*Acting Director of the United States Patent and Trademark Office*